United States Patent
Kane et al.

(12) 
(10) Patent No.: US 11,185,644 B2
(45) Date of Patent: Nov. 30, 2021

(54) FILTER CARTRIDGE ASSEMBLIES

(71) Applicant: Conmed Corporation, Utica, NY (US)

(72) Inventors: Michael J. Kane, Clinton, CT (US);
Michael J. Augelli, Prospect, CT (US);
Mikiya Silver, New Haven, CT (US)

(73) Assignee: Conmed Corporation, Utica, NY (US)

( * ) Notice: Subject to any disclaimer, the term of this patent is extended or adjusted under 35 U.S.C. 154(b) by 466 days.

(21) Appl. No.: 15/988,702

(22) Filed: May 24, 2018

(65) Prior Publication Data
US 2019/0001078 A1 Jan. 3, 2019

Related U.S. Application Data

(60) Provisional application No. 62/527,553, filed on Jun. 30, 2017.

(51) Int. Cl.
*A61M 13/00* (2006.01)
*B01D 46/52* (2006.01)
(Continued)

(52) U.S. Cl.
CPC ........ *A61M 13/003* (2013.01); *A61M 13/006* (2014.02); *B01D 46/0008* (2013.01); *B01D 46/0023* (2013.01); *B01D 46/0031* (2013.01); *B01D 46/0036* (2013.01); *B01D 46/12* (2013.01); *B01D 46/521* (2013.01); *B01D 53/0407* (2013.01); *A61M 16/0808* (2013.01);
(Continued)

(58) Field of Classification Search
None
See application file for complete search history.

(56) References Cited

U.S. PATENT DOCUMENTS

| 5,047,072 A | * | 9/1991 | Wertz | ........................ B08B 5/04 |
| | | | | 95/90 |
| 6,576,033 B1 | * | 6/2003 | Booth | .................. B01D 46/002 |
| | | | | 428/36.1 |

(Continued)

FOREIGN PATENT DOCUMENTS

| CN | 101448545 A | 6/2009 |
| CN | 102264451 A | 11/2011 |

(Continued)

OTHER PUBLICATIONS

PCT International Search Report and Written Opinion dated Sep. 28, 2018, issued during the prosecution of PCT International Patent Application No. PCT/US2018/034632 (13 pages).

(Continued)

*Primary Examiner* — Bobby Ramdhanie
*Assistant Examiner* — Brit E. Anbacht
(74) *Attorney, Agent, or Firm* — Locke Lord LLP; Scott D. Wofsy; Joshua L. Jones

(57) ABSTRACT

A filter cartridge for surgical gas delivery systems includes a filter housing configured to be seated in a filter cartridge interface of a surgical gas delivery system. A first filter element is seated in a first end portion of the filter housing. A second filter element is seated in a second end portion of the filter housing opposite the first end portion. A third filter element is seated in the filter housing between the first and second filter elements. The third filter element can include an activated carbon material, such as an activated carbon disc.

17 Claims, 4 Drawing Sheets

(51) Int. Cl.
  *B01D 46/00*     (2006.01)
  *B01D 46/12*     (2006.01)
  *B01D 53/04*     (2006.01)
  *A61M 16/08*     (2006.01)

(52) U.S. Cl.
  CPC . *A61M 16/0858* (2014.02); *A61M 2202/0225* (2013.01); *A61M 2205/125* (2013.01); *A61M 2205/505* (2013.01); *A61M 2205/6018* (2013.01); *A61M 2205/75* (2013.01); *A61M 2205/7545* (2013.01); *B01D 2253/102* (2013.01); *B01D 2271/02* (2013.01)

(56) References Cited

U.S. PATENT DOCUMENTS

| | | | | |
|---|---|---|---|---|
| 6,685,665 | B2* | 2/2004 | Booth | A61B 17/3421 604/158 |
| 7,182,752 | B2* | 2/2007 | Stubbs | A61B 17/3421 604/164.01 |
| 7,285,112 | B2* | 10/2007 | Stubbs | A61B 17/3423 604/167.01 |
| 7,338,473 | B2* | 3/2008 | Campbell | A61B 17/3421 604/164.01 |
| 7,413,559 | B2 | 8/2008 | Stubbs et al. | |
| 7,854,724 | B2* | 12/2010 | Stearns | A61B 17/3474 604/167.01 |
| 8,608,816 | B2* | 12/2013 | Palmerton | A61M 1/0001 55/319 |
| 9,387,295 | B1* | 7/2016 | Mastri | B01D 46/0008 |
| 2002/0166811 | A1 | 11/2002 | Walker et al. | |
| 2004/0194441 | A1* | 10/2004 | Kirsch | B01D 46/521 55/497 |
| 2011/0308524 | A1* | 12/2011 | Brey | B01D 46/0027 128/205.12 |
| 2012/0198804 | A1* | 8/2012 | Kaiser | B01D 46/10 55/486 |
| 2013/0125757 | A1* | 5/2013 | Patel | B01D 46/0023 96/154 |
| 2013/0231606 | A1* | 9/2013 | Stearns | B01D 46/0008 604/26 |
| 2015/0047507 | A1* | 2/2015 | Fox | B01D 46/0032 96/74 |
| 2015/0047508 | A1* | 2/2015 | Sanocki | B01D 46/0001 96/74 |
| 2015/0306536 | A1* | 10/2015 | Billingsley | B01J 20/06 128/205.29 |
| 2016/0220768 | A1 | 8/2016 | Mastri et al. | |
| 2016/0287817 | A1* | 10/2016 | Mastri | A61M 5/165 |
| 2017/0281255 | A1* | 10/2017 | Babini | A61B 18/00 |
| 2018/0339262 | A1* | 11/2018 | Perl-Olshvang | F24F 3/16 |
| 2019/0001078 | A1* | 1/2019 | Kane | B01D 50/002 |
| 2019/0308127 | A1* | 10/2019 | Ferguson | B01D 46/528 |
| 2019/0388631 | A1* | 12/2019 | Silver | B01D 46/521 |

FOREIGN PATENT DOCUMENTS

| | | |
|---|---|---|
| CN | 106731319 A | 5/2017 |
| JP | 2000070627 A | 3/2000 |
| JP | 2013541972 A | 11/2013 |
| JP | 5829955 B2 | 12/2015 |
| WO | 2010/042914 A2 | 4/2010 |
| WO | 2012/040221 A2 | 3/2012 |

OTHER PUBLICATIONS

Supplementary European Search Report issued in EP 18822606, dated Jan. 6, 2021.
Japanese Office Action dated Feb. 9, 2021, issued during the prosecution of Japanese Patent Application No. 2019-572381.
Canadian Examination Report dated Jan. 27, 2021, issued during the prosecution of Canadian Patent Application No. CA 3067207.
Chinese Office Action (and English translation thereof) dated Jul. 6, 2021, issued during the prosecution of Chinese Patent Application No. CN 201880053262.0. (22 pages).

* cited by examiner

FILTER CARTRIDGE ASSEMBLIES

CROSS-REFERENCE TO RELATED APPLICATIONS

This application claims benefit of priority to U.S. Provisional Patent Application No. 62/527,553 filed Jun. 30, 2017 which is incorporated by reference herein in its entirety.

BACKGROUND OF THE INVENTION

1. Field of the Invention

The subject invention is directed to laparoscopic surgery, and more particularly, to a filter cartridge for a multimodal insufflation system used during laparoscopic surgical procedures.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a surgical access device (sometimes referred to as a "cannula" or "trocar") equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, typically using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain the pressure within the cavity by sealing between the trocar and the surgical instrument being used, while still allowing at least a minimum freedom of movement of the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas. Sealing elements or mechanisms typically include a duckbill-type valve made of a relatively pliable material, to seal around an outer surface of surgical instruments passing through the trocar.

Further, in laparoscopic surgery, electrocautery and other techniques (e.g. harmonic scalpels) create smoke and other debris in the surgical cavity, reducing visibility by fogging the view from, and coating surfaces of endoscopes and the like. A variety of surgical insufflation systems and smoke evacuation systems are known in the art.

Additionally, CONMED Corporation of Utica, N.Y., USA has developed surgical access devices that permit access to an insufflated surgical cavity without conventional mechanical seals, and has developed related systems for providing sufficient pressure and flow rates to such access devices, as described in whole or in part in U.S. Pat. No. 7,854,724.

The present disclosure relates to multimodal systems, and related devices and methods, capable of performing multiple surgical gas delivery functions, including insufflation to standard or specialized surgical access devices or other instruments, such as veress needles and the like, smoke evacuation through standard or specialized surgical access devices, and specialized functions, such as recirculation and filtration of insufflation fluids, such as with the above-mentioned surgical access devices described in U.S. Pat. No. 7,854,724, as well as those in U.S. Pat. Nos. 7,182,752, 7,285,112, 7,413,559 or 7,338,473, for example.

Use of a single multimodal system such as those described herein reduces costs by requiring purchase of only one system while achieving multiple functions, and also thereby reduces the amount of equipment needed in an operating room, thus reducing clutter and allowing space for other necessary equipment.

The conventional techniques have been considered satisfactory for their intended purpose. However, there is an ever present need for improved filtration in surgical access devices. This disclosure provides a solution for this problem.

SUMMARY OF THE INVENTION

A filter cartridge for surgical gas delivery systems includes a filter housing configured to be seated in a filter cartridge interface of a surgical gas delivery system. A first filter element is seated in a first end portion of the filter housing. A second filter element is seated in a second end portion of the filter housing opposite the first end portion. A third filter element is seated in the filter housing between the first and second filter elements.

The third filter element can include an activated carbon material. The third filter element can include an activated carbon disc. Each of the first and second filter elements can include a pleated filter material. The second filter element can be in a flow path downstream of the third filter element. The first filter element can be in a separate flow path from the second and third filter elements.

A separator wall can be included within the filter housing between the first filter element and the second filter element. The separator wall can include a gas aperture therethrough, wherein a plenum is defined between the separator wall and the third filter element, and wherein the gas aperture is configured to pressurize the plenum with gas for utilization of a larger cross-sectional area of the third filter element than that of the gas aperture. A peripheral rim can be defined around the separator wall, wherein the third filter element seats against the peripheral rim to maintain the plenum defined inside a volume defined between the separator wall and the third filter element and within the peripheral rim. A seal can be seated between the separator wall and the third filter element to force gas flow from the plenum through the third filter element. A seal seat can be defined in the peripheral rim with the seal seated therein. A fluid trap can be defined between the first filter element and the separator wall, wherein the gas aperture is configured to allow passage of gas above a reservoir of fluid trapped in the fluid trap.

A cover plate can be mounted to the filter housing to secure the first filter element in the first end portion of the filter housing. The cover plate can include a fitting for connecting to a tri-lumen tube set for communication of gases between a tri-lumen tube set and the filter elements. A tri-lumen tube set can be connected to the fitting. It is also contemplated that the cover plate can include a fitting for connecting to a bi-lumen tube set for communication of gases between a bi-lumen tube set and the filter elements. A bi-lumen tube set can be connected to the fitting.

A second cover plate can be mounted to the filter housing to secure the second filter element in the second end portion of the filter housing. The second cover plate can define three apertures configured to seal against three respective gas ports defined in a filter cartridge interface of a surgical gas delivery system.

Another exemplary embodiment of a filter cartridge for surgical gas delivery systems includes a filter housing configured to be seated in a filter cartridge interface of a surgical gas delivery system. A first filter element is seated in a first end portion of the filter housing in a first flow path. A second filter element seated in a second end portion of the filter housing opposite the first end portion in a second flow path. A third filter element is seated in the filter housing between the first and second filter elements, wherein the third filter element is in the second flow path, wherein the first and second flow paths are fluidly isolated from one another within the filter housing. A fourth filter element can be seated in a third flow path that is fluidly isolated from the first and second flow paths within the filter housing.

A method of processing surgical gas for a surgical gas delivery system includes receiving smoke evacuation gas from a pneumoperitoneum into a filter cartridge. The method includes flowing the smoke evacuation gas through an activated carbon filter element within the filter cartridge to filter at least one of smoke, particulate, and impurities from the smoke evacuation gas. The method also includes receiving the filtered smoke evacuation gas into a surgical gas delivery system.

The method can include flowing the smoke evacuation gas through a pleated filter element downstream of the activated carbon filter element and upstream of the surgical gas delivery system. It is also contemplated that the method can include flowing insufflation gas into the pneumoperitoneum through a separate flow path in the filter cartridge from the smoke evacuation gas, wherein the insufflation gas passes through a second pleated filter element in the filter cartridge, and communicating pressure from the pneumoperitoneum through a third flow path through the filter cartridge separate from the flow paths of the insufflation gas and smoke evacuation gas.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
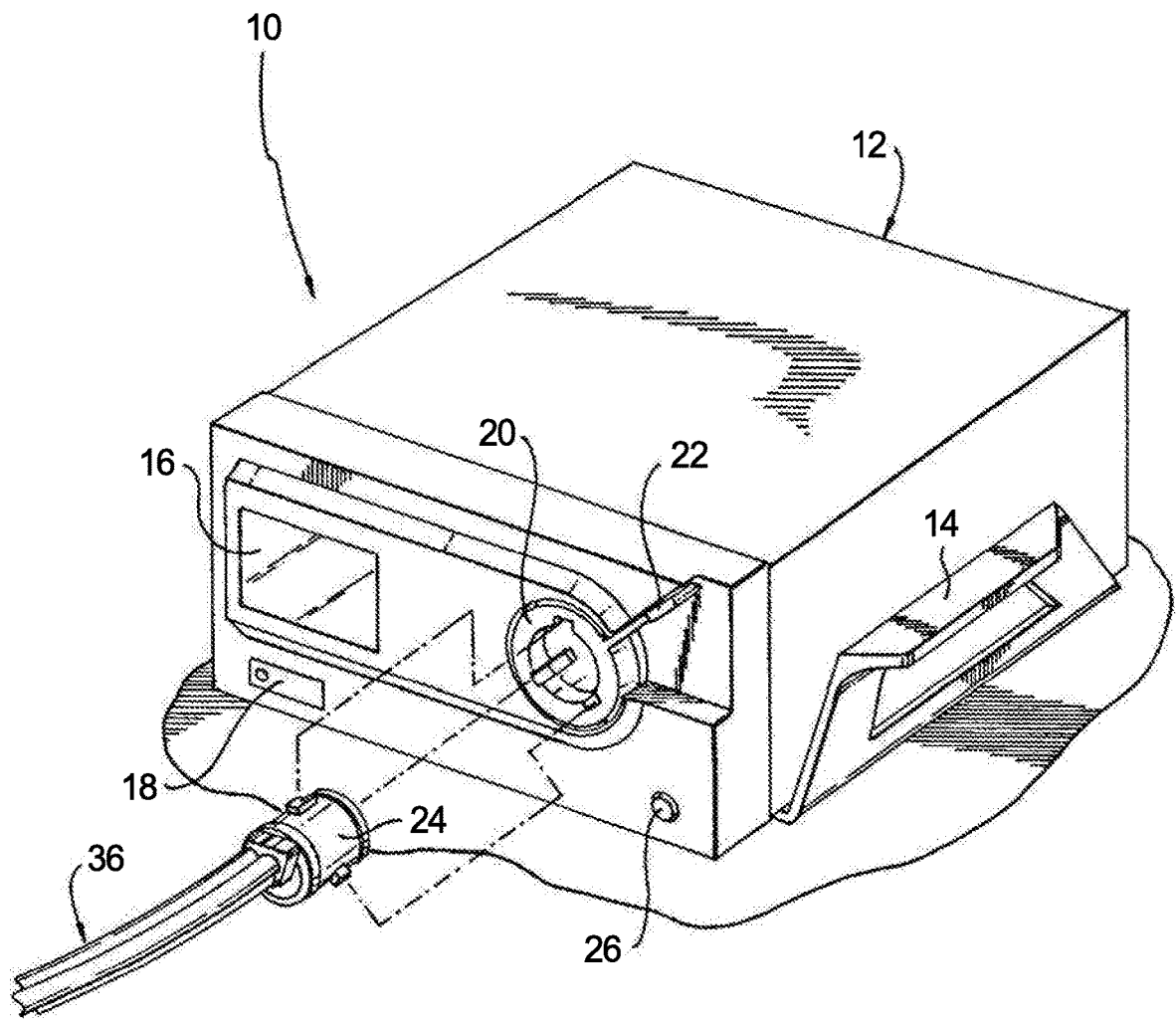
FIG. 1 is a perspective view of a multimodal gas delivery device constructed in accordance with an exemplary embodiment of the subject invention, showing the filter cartridge and the corresponding filter cartridge interface.

Reference will now be made to the drawings wherein like reference numerals identify similar structural features or aspects of the subject disclosure. For purposes of explanation and illustration, and not limitation, a partial view of an exemplary embodiment of a filter cartridge in accordance with the disclosure is shown in FIG. 1 and is designated generally by reference character 100. Other embodiments of filter cartridges in accordance with the disclosure, or aspects thereof, are provided in FIGS. 2-4, as will be described. The systems and methods described herein can be used for filtering surgical gases such as smoke evacuation gas from a pneumoperitoneum during smoke-producing surgical procedures.

There is illustrated in FIG. 1 a surgical gas delivery system 10 for use during laparoscopic surgical procedures. The system 10 includes a device housing 12 with carrying handles 14 on each side of the housing. The front face of the housing 12 has a capacitive or resistive touch screen 16 for presenting a graphical user interface (GUI) and a power switch 18 for turning the device on and off.

The front face of housing 12 further includes a filter cartridge interface 20 with a rotatable latch mechanism 22 configured to facilitate the secure engagement of a disposable filter cartridge 24 within the device housing 12. In addition, the front face of housing 12 includes a standard 6 mm insufflation connection 26. While not shown, the rear face of the housing 12 includes a gas supply fitting for connection with a source of compressed gas, a standard USB interface for service purposes, and a standard power connection.

The filter cartridge interface 20 is designed to recognize which type of filter 24 has been inserted into the housing. For example, it may recognize the proper position or orientation of the filter cartridge. It can also recognize if the inserted filter is specifically designed for use in the first mode of operation (i.e., the gaseous seal mode) or a filter specifically designed for use in the second mode of operation (i.e., insufflation and smoke evacuation mode). Other aspects of surgical gas delivery systems are described in U.S. Pat. No. 9,067,030, which is incorporated by reference herein in its entirety.

Figure 2:
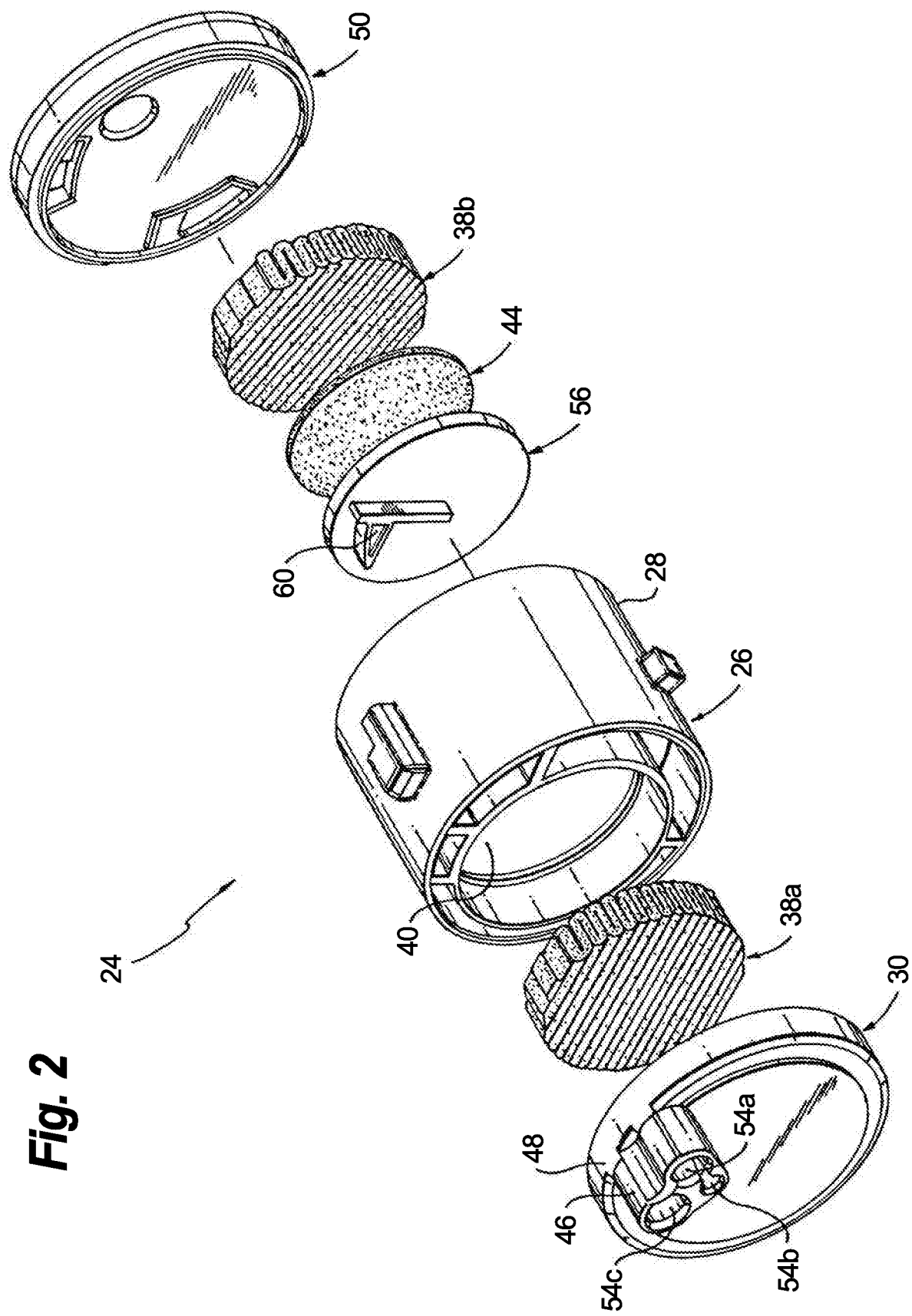
FIG. 2 is an exploded perspective view of a filter cartridge adapted and configured for interfacing with the gas delivery device of FIG. 1, showing the filter cartridge components looking toward the openings in the fitting for the tri-lumen-tube set in the first cover plate.

Referring to FIG. 2, the filter cartridge 24 has a filter housing 28 that includes a first cover plate 30 having a fitting 46 associated with a tri-lumen tube set 36 (as shown in FIG. 1). The filter housing 28 is configured to be seated in the filter cartridge interface 20 of the surgical gas delivery system 10 of FIG. 1. The filter housing 28 is dimensioned and configured to support a pair of first and second pleated filter elements 38a and 38b, and it defines an interior reservoir or fluid trap 40 for collecting liquid that has been drawn into the system through the suction line of the tube set 36 during smoke evacuation, for example.

Figure 3:
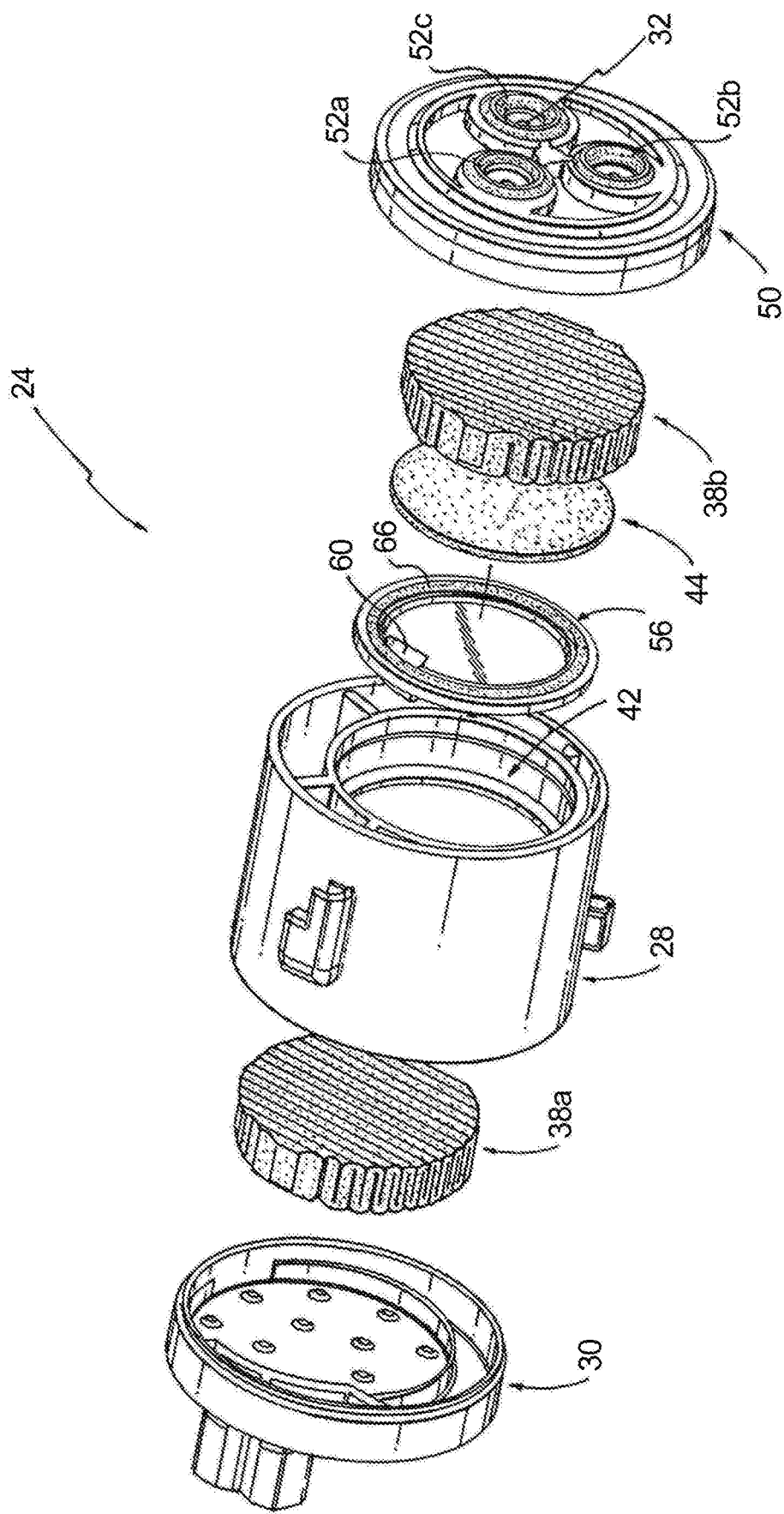
FIG. 3 is an exploded perspective view of the filter cartridge of FIG. 1, showing the filter cartridge components looking toward the apertures in the second cover plate that seal against the gas ports in the filter cartridge interface of FIG. 1.
Figure 4:
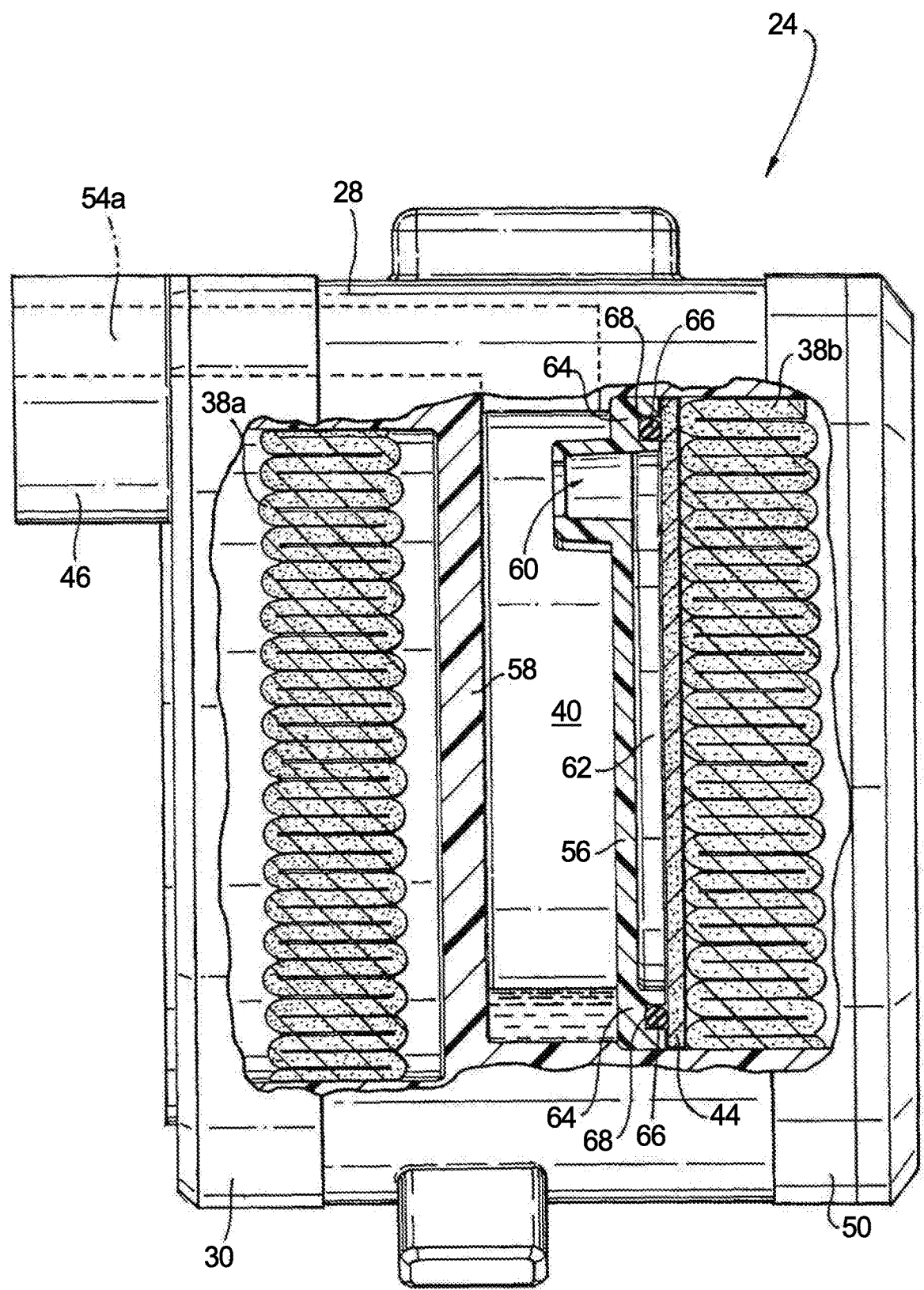
FIG. 4 is a cross-sectional side elevation view of the filter cartridge of FIG. 1, showing the filter elements assembled into the filter housing.

The first filter element 38a is seated in a first end portion 26 of the filter housing 28. As shown in FIG. 3, the second filter element 38b is seated in a second end portion 42 of the filter housing 28 opposite the first end portion 26. A third filter element 44 is seated in the filter housing 28 between the first and second filter elements 38a and 38b, as shown in FIG. 4. There is a fourth filter element 32 within end cap 50, shown in FIG. 3, that is a non-pleated filter for the sense/insufflation line described below. The third filter element 44 includes an activated carbon material and is in the form of an activated carbon disc. Each of the first and second filter elements 38a and 38b includes a pleated filter material. The third filter element 44 is a separate filter element from the second and third filter elements 38a and 38b, but it is contemplated that it could be integrated together with the second filter element 38b. For example, a mesh support can be sandwiched between a paper filter and a carbon filter together that can then be folded into pleats to form combined second filter element 38b and third filter element 44.

The first cover plate 30 is mounted to a first end of the filter housing 28 to secure the first filter element 38a in the first end portion 26 of the filter housing 28. The first cover plate 30 includes a fitting 46 for connecting to the tri-lumen tube set 36 for communication of gases between a tri-lumen tube set 36 and the filter elements 38a, 38b, and 44. A second cover plate 50 is mounted to the opposite end of the filter housing 28 to secure the second filter element 38b in the second end portion 42 of the filter housing. The second cover plate 50 includes a proximal and a distal plate welded or otherwise joined together with the fourth filter element 32 sandwiched therebetween. Referring to FIG. 3, the second cover plate 50 defines three apertures 52a, 52b, and 52c that are each configured to seal against three respective gas ports defined in the filter cartridge interface 20 of FIG. 1. Fitting 46 includes three corresponding openings 54a, 54b, and 54c.

A first flow path is defined through filter cartridge 24 from opening 54a, through to fluid trap 40 (as indicated with broken lines in FIG. 4) and on through the second and third filter elements 38b and 44 and out through aperture 52a for filtration of smoke evacuation gas from a pneumoperitoneum, through one of lumens in the tri-lumen tube set 36 into the surgical gas delivery system 10. The second filter element 38b is downstream of the third filter element 44 in this first flow path.

A second flow path is defined through the filter cartridge 24, that is fluidly isolated within the filter cartridge 24 from the first flow path. The second flow path brings gas from the surgical gas delivery system 10, through aperture 52b, through the first filter element 38a, and out opening 54b for maintaining a pneumoperitoneum with gas through a second one of the lumens in the tri-lumen tube set 36. The first filter element 38a is therefore in a separate flow path from the second and third filter elements 38b and 44. This second flow path is in the pressure line, supplying pressure to jets to create a gas seal in a valve-less seal, e.g., for a surgical access device connected to the tri-lumen tube set 36.

A third flow path is defined through the filter cartridge 24 that is fluidly isolated within the filter cartridge 24 from the other two flow paths. This third flow path does not pass through any of the filter elements 38a, 38b, or 44. Instead, the third flow path communicates abdominal pressure from opening 54c through the filter cartridge 24 to aperture 52c, bypassing the filter elements 38a, 38b, and 44 so the surgical gas delivery system 10 can monitor pressure in the pneumoperitoneum through a third one of the lumens in the tri-lumen tube set 36. $CO_2$ insufflation gas can flow from aperture 52c to opening 54c to a pneumoperitoneum. This third flow path acts as the insufflation/sense line, and is the only one of the three flow paths that passes through the fourth filter element 32.

With reference now to FIG. 4, a separator wall 56 is included within the filter housing 28 between the first filter element 38a and the second filter element 38b. The separator wall 56 cooperates with a bulkhead 58 of filter housing 28 inboard of first filter element 38a to define the fluid trap 40 therebetween for trapping fluids (shown schematically in FIG. 4 in the bottom of the fluid trap 40) from incoming gas from the pneumoperitoneum. The separator wall 56 includes a gas aperture 60 therethrough. The gas aperture 60 is configured to allow passage of gas above a reservoir of fluid trapped in the bottom of fluid trap 40.

A plenum 62 is defined between the separator wall 56 and the third filter element 44. The gas aperture 60 is configured to pressurize the plenum 62 with gas for utilization of a larger cross-sectional area of the third filter element 44 than the cross-sectional area of the gas aperture 60, i.e. the plenum 62 is pressurized for nearly full area usage of the activated carbon of the third filter element 44. This allows flowing the smoke evacuation gas through the activated carbon filter element 44 within the filter cartridge 24 to filter at least one of smoke, particulate, and impurities from the smoke evacuation gas.

A peripheral rim 64 is defined around the separator wall 56, wherein the third filter element 44 seats against the peripheral rim 64 to maintain spacing for the plenum 62 defined inside a volume defined between the separator wall 56 and the third filter element 44 and within the peripheral rim 64. A seal 66 is seated between the separator wall 56 and the third filter element 44 to force gas flow from the plenum 62 through the third filter element 44. A seal seat 68 is defined in the peripheral rim 64 with the seal 66 seated therein.

Another embodiment of a filter with tube set in accordance with this disclosure includes an adapter that plugs the pressure line, e.g., by plugging opening 54b, which is responsible for creating the gas seal described above. In this embodiment, a bi-lumen tube set would be attached to the filter cartridge, e.g., with one lumen connected to opening 54a and one lumen connected to opening 54c, with one lumen responsible for sense/insufflation gas, and the other lumen removing surgical gas and smoke from the cavity. This embodiment includes the third filter element 44 as described above for smoke evacuation, and omits the third lumen of the tri-lumen tube set 36.

The methods and systems of the present disclosure, as described above and shown in the drawings, provide for filtration of surgical gases with superior properties including improved removal of smoke, particulate, and impurities. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A filter cartridge for surgical gas delivery systems comprising: a filter housing configured to be seated in a filter cartridge interface of a surgical gas delivery system; a first filter element seated in a first end portion of the filter housing; a second filter element seated in a second end portion of the filter housing opposite the first end portion;

and a third filter element seated in the filter housing between the first and second filter elements, wherein the third filter element includes a non-pleated activated carbon disc, wherein a first flow path brings smoke evacuation gas from a peritoneal cavity to the surgical gas delivery system and a second flow path brings gas from the surgical gas delivery system to the peritoneal cavity, wherein the second filter element is in the first flow path downstream of the third filter element and the first filter element is in the second flow path, separate from the second and third filter elements.

2. A filter cartridge as recited in claim 1, wherein each of the first and second filter elements includes a pleated filter material.

3. A filter cartridge as recited in claim 1, further comprising a separator wall within the filter housing between the first filter element and the second filter element.

4. A filter cartridge as recited in claim 3, wherein the separator wall includes a gas aperture therethrough, wherein a plenum is defined between the separator wall and the third filter element, wherein the gas aperture is configured to pressurize the plenum with gas for utilization of a larger cross-sectional area of the third filter element than that of the gas aperture.

5. A filter cartridge as recited in claim 4, wherein a peripheral rim is defined around the separator wall, wherein the third filter element seats against the peripheral rim to maintain the plenum defined inside a volume defined between the separator wall and the third filter element and within the peripheral rim.

6. A filter cartridge as recited in claim 5, wherein a seal is seated between the separator wall and the third filter element to force gas flow from the plenum through the third filter element.

7. A filter cartridge as recited in claim 6, wherein a seal seat is defined in the peripheral rim with the seal seated therein.

8. A filter cartridge as recited in claim 4, wherein a fluid trap is defined between the first filter element and the separator wall, wherein the gas aperture is configured to allow passage of gas above a reservoir of fluid trapped in the fluid trap.

9. A filter cartridge as recited in claim 1, further comprising a cover plate mounted to the filter housing to secure the first filter element in the first end portion of the filter housing.

10. A filter cartridge as recited in claim 9, wherein the cover plate includes a fitting for connecting to a tri-lumen tube set for communication of gases between a tri-lumen tube set and the filter elements.

11. A filter cartridge as recited in claim 10, further comprising a tri-lumen tube set connected to the fitting.

12. A filter cartridge as recited in claim 9, wherein the cover plate includes a fitting for connecting to a bi-lumen tube set for communication of gases between a bi-lumen tube set and the filter elements.

13. A filter cartridge as recited in claim 12, further comprising a bi-lumen tube set connected to the fitting.

14. A filter cartridge as recited in claim 1, further comprising a cover plate mounted to the filter housing to secure the second filter element in the second end portion of the filter housing.

15. A filter cartridge as recited in claim 14, wherein the cover plate defines three apertures configured to seal against three respective gas ports defined in a filter cartridge interface of a surgical gas delivery system.

16. A filter cartridge for surgical gas delivery systems comprising: a filter housing configured to be seated in a filter cartridge interface of a surgical gas delivery system; a first filter element seated in a first end portion of the filter housing in a first flow path; a second filter element seated in a second end portion of the filter housing opposite the first end portion in a second flow path; and a third filter element seated in the filter housing between the first and second filter elements, wherein the third filter element is in the second flow path and is a non-pleated activated carbon disc, wherein the first and second flow paths are fluidly isolated from one another within the filter housing, wherein the first flow path brings smoke evacuation gas from a peritoneal cavity to the surgical gas delivery system and the second flow path brings gas from the surgical gas delivery system to the peritoneal cavity, wherein the second filter element is downstream of the third filter element.

17. A filter cartridge as recited in claim 16, further comprising a fourth filter element seated in a third flow path that is fluidly isolated from the first and second flow paths within the filter housing.

* * * * *